United States Patent
Nagahama et al.

(10) Patent No.: US 8,908,740 B2
(45) Date of Patent: Dec. 9, 2014

(54) LIGHT EMITTING DEVICE

(75) Inventors: Shinichi Nagahama, Tokushima (JP); Atsutomo Hama, Anan (JP); Takafumi Sugiyama, Kamatsushima (JP); Tomohisa Kishimoto, Anan (JP)

(73) Assignee: Nichia Corporation, Anan-shi (JP)

( * ) Notice: Subject to any disclaimer, the term of this patent is extended or adjusted under 35 U.S.C. 154(b) by 1236 days.

(21) Appl. No.: 11/702,598

(22) Filed: Feb. 6, 2007

(65) Prior Publication Data

US 2007/0189352 A1 Aug. 16, 2007

(30) Foreign Application Priority Data

Feb. 14, 2006 (JP) .................................. 2006-036258
Mar. 23, 2006 (JP) .................................. 2006-081524

(51) Int. Cl.
*H01S 3/08* (2006.01)
*C09K 11/77* (2006.01)
*A61B 1/06* (2006.01)

(52) U.S. Cl.
CPC ........... *C09K 11/7734* (2013.01); *A61B 1/0653* (2013.01); *C09K 11/7738* (2013.01); *C09K 11/7741* (2013.01); *C09K 11/7774* (2013.01); *C09K 11/7789* (2013.01)
USPC .......... 372/108; 372/21; 362/84; 362/217.08; 362/260; 362/574; 606/15; 606/16; 607/93

(58) Field of Classification Search
USPC ......... 372/21, 108; 362/574, 84, 217.08, 260; 606/15, 16; 607/93
See application file for complete search history.

(56) References Cited

U.S. PATENT DOCUMENTS

| | | | |
|---|---|---|---|
| 5,289,491 A * | 2/1994 | Dixon .............................. | 372/92 |
| 5,696,781 A * | 12/1997 | Hyuga .............................. | 372/21 |
| 5,982,789 A * | 11/1999 | Marshall et al. ................. | 372/22 |
| 6,212,213 B1 | 4/2001 | Weber et al. | |
| 6,876,412 B2 | 4/2005 | Udaka et al. | |
| 7,057,683 B2 | 6/2006 | Udaka et al. | |
| 7,083,610 B1 * | 8/2006 | Murray et al. ..................... | 606/9 |
| 7,453,568 B2 | 11/2008 | Kawamata et al. | |
| 7,705,326 B2 | 4/2010 | Kawamata et al. | |
| 2003/0072335 A1 * | 4/2003 | Momiuchi et al. .............. | 372/21 |
| 2004/0012753 A1 | 1/2004 | Udaka et al. | |
| 2004/0061433 A1 * | 4/2004 | Izuno et al. .................... | 313/498 |
| 2005/0078265 A1 | 4/2005 | Udaka et al. | |
| 2005/0105301 A1 * | 5/2005 | Takeda et al. ................. | 362/545 |
| 2006/0017913 A1 | 1/2006 | Kawamata et al. | |
| 2006/0165145 A1 * | 7/2006 | Krupke ........................... | 372/70 |

(Continued)

FOREIGN PATENT DOCUMENTS

| | | |
|---|---|---|
| JP | H09-049922 A | 2/1997 |
| JP | H11-064789 A | 3/1999 |

(Continued)

*Primary Examiner* — Tod T Van Roy
(74) *Attorney, Agent, or Firm* — Global IP Counselors, LLP

(57) ABSTRACT

A light emitting device, comprises: a light source that emits excitation light; a light guide that propagates the excitation light, and in which the refractive index of the center part (core) of a cross section is higher than the refractive index of the peripheral part (cladding); a wavelength conversion member that absorbs the excitation light propagated by the light guide and converts the wavelength thereof, and releases light of a predetermined wavelength band; and a shielding member that blocks the wavelength of at least part of the excitation light and the light emitted from the wavelength conversion member.

17 Claims, 10 Drawing Sheets

(56) References Cited

U.S. PATENT DOCUMENTS

| | | |
|---|---|---|
| 2008/0231170 A1 | 9/2008 | Masato et al. |
| 2008/0262316 A1 | 10/2008 | Ajima et al. |
| 2008/0296511 A1 | 12/2008 | Kawamata et al. |

FOREIGN PATENT DOCUMENTS

| | | |
|---|---|---|
| JP | 2000-223745 A | 8/2000 |
| JP | 2000-231851 A | 8/2000 |
| JP | 2002-365621 A | 12/2002 |
| JP | 2003-233123 A | 8/2003 |
| JP | 2003-287802 A | 10/2003 |
| JP | 2004-71357 A | 3/2004 |
| JP | 2004-080046 A | 3/2004 |
| JP | 2004-231737 A | 8/2004 |
| JP | 2005-005482 A | 1/2005 |
| JP | 2005-093896 A | 4/2005 |
| JP | 2005-106801 A | 4/2005 |
| JP | 2005-205195 A | 8/2005 |
| JP | 2005-319212 A | 11/2005 |
| JP | 2005-328921 A | 12/2005 |
| JP | 2005-347223 A | 12/2005 |
| JP | 2006-061685 A | 3/2006 |
| WO | WO-03/021329 A2 | 3/2003 |
| WO | WO-2005/071039 A1 | 8/2005 |
| WO | WO-2006/011571 A1 | 2/2006 |
| WO | WO-2006/038502 A1 | 4/2006 |

* cited by examiner

LIGHT EMITTING DEVICE

BACKGROUND OF THE INVENTION

1. Field of the Invention

The present invention relates to a light emitting device, and more particularly to a light emitting device that can be utilized in laser displays, projector devices, endoscopes, and so forth.

2. Background Information

With laser displays, projector devices, endoscopes, and so forth, light of various wavelengths is combined to produce light of the desired wavelength (see Japanese Laid-Open Patent Application 2005-205195, for example), and this requires a light emitting device that is capable of emitting the blue, red, green, or other light that is to be combined.

For example, there is a projector device comprising a semiconductor laser (as a solid-state light source that emits blue light with a wavelength of 405 nm), an optical fiber having a core doped with a wavelength downward conversion material for converting excitation light to blue, an optical fiber having a core doped with a wavelength downward conversion material for converting excitation light to green, an optical fiber having a core doped with a wavelength downward conversion material for converting excitation light to red, a converging lens and a projection lens for guiding the light emitted from the optical fibers to a liquid crystal panel, and the liquid crystal panel, wherein the liquid crystal panel performs processing in which the desired image is displayed on a screen by using the red, blue, and green light emitted from the optical fibers, respectively (see Japanese Laid-Open Patent Application 2003-233123, for example).

With this light emitting device, the light source may in some cases be an LED, but a problem with an LED is its low brightness. Also, the light source may in some cases be an SHG laser or other such solid-state laser or a gas laser, but because these entail a complicated structure, the light emitting device becomes large and power consumption goes up.

It is therefore believed to be preferable for the light source to be a laser diode, but so far no laser diode that emits green light has been developed (there are laser diodes that emit a green component, but green does not result from color mixing). Thus, when the light source consists of a laser diode, it is necessary to obtain green from a laser diode that emits light of another color besides green.

Also, it will be necessary in the future to further increase the luminous flux emitted from a light emitting device, but at the present time the luminous flux of emitted light is not large enough to meet future needs.

SUMMARY OF THE INVENTION

It is an object of the present invention to provide a novel light emitting device that has high brightness and is suited to reducing the size, has reduced power consumption, and emits green light using a laser diode as a light source.

It is another object of the present invention to provide a novel light emitting device can be provided with which it is possible to increase the luminous flux that is emitted.

The present invention provides first light emitting device, comprising:

a light source that emits excitation light;

a light guide that propagates the excitation light, and in which the refractive index of the center part (core) of a cross section is higher than the refractive index of the peripheral part (cladding);

a wavelength conversion member that absorbs the excitation light propagated by the light guide and converts the wavelength thereof, and releases light of a predetermined wavelength band; and a shielding member that blocks the wavelength of at least part of the excitation light and the light emitted from the wavelength conversion member.

Further, the present invention provides second light emitting device, comprising:

at least one first light source that emits light whose emission peak wavelength is in a wavelength band of 400 to 500 nm;

at least one second light source that emits light whose emission peak wavelength is in a wavelength band of 600 to 700 nm;

a first light guide having at least one optical fiber for propagating the light emitted by the first light source, in which the refractive index of the center part (core) of a cross section is higher than the refractive index of the peripheral part (cladding);

a second light guide having at least one optical fiber for propagating the light emitted by the second light source, in which the refractive index of the center part (core) of a cross section is higher than the refractive index of the peripheral part (cladding);

a wavelength conversion member that is provided to just the end on the emission side of the first light guide, or to both the end on the emission side of the first light guide and the end on the emission side of the second light guide, absorbs the light propagated by the first light guide and converts the wavelength thereof, and releases light having an emission peak wavelength in a wavelength band of 450 to 650 nm.

Moreover, the present invention provides third light emitting device, comprising:

at least one first light source that emits light whose emission peak wavelength is in a wavelength band of 400 to 500 nm;

at least one second light source that emits light whose emission peak wavelength is in a wavelength band of 600 to 700 nm;

at least one third light source that emits light whose emission peak wavelength is in a wavelength band of 300 to 400 nm;

a first light guide having at least one optical fiber for propagating the light emitted by the first light source, in which the refractive index of the center part (core) of a cross section is higher than the refractive index of the peripheral part (cladding);

a second light guide having at least one optical fiber for propagating the light emitted by the second light source, in which the refractive index of the center part (core) of a cross section is higher than the refractive index of the peripheral part (cladding);

a third light guide having at least one optical fiber for propagating the light emitted by the third light source, in which the refractive index of the center part (core) of a cross section is higher than the refractive index of the peripheral part (cladding);

a wavelength conversion member that is provided to just the end on the emission side of the third light guide, or to both the end on the emission side of the first light guide and the end on the emission side of the third light guide, or to the end on the emission side of the first light guide, the end on the emission side of the second light guide, and the end on the emission side of the third light guide, absorbs the light propagated by the third light guide and converts the wavelength thereof, and releases light having an emission peak wavelength in a wavelength band of 450 to 650 nm.

With the present invention, since light of a specific wavelength can be taken out from a light emitting device, it is possible to provide a novel light emitting device that has high brightness and is suited to reducing the size, has reduced power consumption, and emits green light using a laser diode as a light source. Also, with the present invention, a novel light emitting device can be provided with which it is possible to increase the flux of light that is emitted.

DETAILED DESCRIPTION OF THE PREFERRED EMBODIMENTS

Embodiment 1

Figure 1:
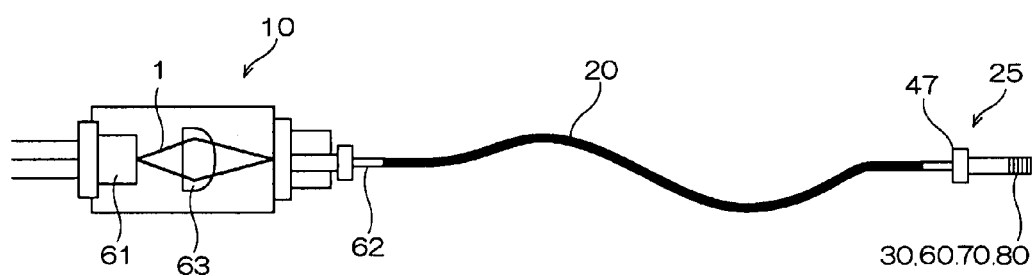
FIG. 1 is a simplified diagram of the light emitting device pertaining to Embodiment 1 of the present invention.

As shown in FIG. 1, the light emitting device of the present invention mainly comprises a light source 10, a light guide 20, a light guide end member 47, a wavelength conversion member 30, a reflection member 60, and a shielding member 70.

Figure 2:
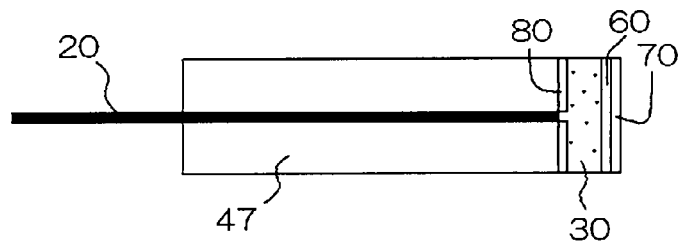
FIG. 2 is a detail view of the exit section 25 in FIG. 1.

As shown in FIG. 2, the light guide end member 47 is provided on the emission side of the light guide 20, and a reflective film 80 that reflects light of a predetermined (specific) wavelength is formed at the end face of this light guide end member 47. The wavelength conversion member 30 is attached to the light guide end member 47 with the reflective film 80 sandwiched in between, the reflection member 60 is attached to the emission side of the wavelength conversion member 30, and the shielding member 70 is attached to the emission side of the reflection member 60.

Light Source 10

The light source 10 emits excitation light, and may emit any light as long as it allows a fluorescent substance (discussed below) to be excited. As shown in FIG. 1, the light source 10 is comprising light emitting elements 61 or the like, and is constructed such that the light emitted from the light emitting elements 61 is guided from the radiating part 62 to the light guide 20. A lens 63 may also be established between the light emitting elements 61 and the radiating part 62. A semiconductor light emitting element, a lamp, or the like, or a device whose energy source is an electron beam, a plasma, electroluminescence, or the like, can be used as a light emitting element 61. Of these, it is preferable to use a light emitting diode element (LED), a laser diode element (LD), or another such light emitting element, with a laser diode element being particularly favorable because of its high emission output and the ease with which light can be put into a light guide.

Light Guide 20

The light guide 20 transfers the light emitted from the light source (light emitting element) 10, and guides the light to the wavelength converting member 30. The light guide 20 may, for instance, be an extremely fine glass fiber which is used as a transfer path for light when transferring the light, and a combination of materials which have a high refraction index and materials which have a low refraction index, or materials which have high reflectivity may be used. Of these materials, double layer materials, in full length of the light guide 20 or a part, with a cross-section where the center part (core) is surrounded by a peripheral part (clad) are preferable, and a material where the refraction index of the core is higher than the refraction index of the clad is more preferable from the viewpoint that a light signal can be transferred without damping. The light guide 20 may be either a monofiber or a multifiber, but a monofiber is preferable. Furthermore, either a single mode fiber or a multimode fiber may be used, but a multimode fiber is preferable.

Light Guide End Member 47

The end of the light guide 20, or in other words the end which is not connected to the light source is preferably supported by a light guide end member. The light emitted from the light guide 20 can easily be fixed by this light guide end member 30. Furthermore, depending on the material and shape thereof, the light emitting efficiency can be increased and the assembly of the light emitting device can be simplified.

The light guide end member 47 may, for instance, have a cylindrical shape in order to cover the outer circumference of the light guide 20, and various functional films or members which provide various functions to the end surface of the light guide 20 may be integrated with or attached separately thereto, or a cover or cap or the like which covers the end surface of the light guide 20 as well as other functional films or members or the like may be integrated with or separately attached thereto.

As shown in FIG. 2, to raise reflectivity, the reflective film 80, which reflects light of a predetermined (specific) wavelength band, may optionally be applied to just the end face of the light guide end member 47 so as to achieve mirror face reflection or scattered reflection, or texturing or other such processing may be performed. As a result, if excitation light emitted from the light guide 20 or wavelength-converted light is reflected back to the light guide 20 side, it will be reflected again by the light guide end member 47, allowing the excitation light and wavelength-converted light to be taken off to the outside more effectively, and increasing the output. The "predetermined (specific) wavelength band" of the light reflected by the reflective film 80 is not limited, as long as the reflective film 80 performs the function outlined above.

Wavelength Conversion Member 30

A wavelength converting member 30 absorbs part or all of the excitation light emitted from the light source, converts the wavelength, and can emit light with a specific wavelength band, having a light emission spectrum containing, for instance, red, green, blue, as well as intermediary colors thereof such as yellow, blue green, and orange or the like. The wavelength converting member 30 is, for instance, constructed from a fluorescent substance or the pigment or the like. The wavelength conversion member may consist of just the above-mentioned fluorescent substance, but if desired, it may be formed by mixing with a resin (for example, one or more types resin of polyolefin, polycarbonate, polystyrene, epoxy, acrylic, acrylate, methacrylic (PMMA or the like), urethane, polyamide, polynorbornene, fluoridated, silicone, modified silicone, modified epoxy, as well as liquid crystal polymer or the like) or other such covering member along with a filler (for example $SiO_2$, $TiO_2$, or the like) that allows light coming in from the outside to be reflected, scattered, and/or diffused, etc. This makes it easier to affix the wavelength conversion member 30 to the light guide 20. It also allows a light emitting device with less color unevenness to be obtained because the wavelength conversion member 30 can be disposed more uniformly.

The wavelength converting member 30 may be formed as a single layer of one type of fluorescent substance or the like, or may be formed as one layer of a uniform mixture of two or more types of fluorescent substances or the like, or may be laminated with two or more layers where each layer contains one type of fluorescent substance or the like, or may be laminated with two or more layers where each layer contains a uniform mixture of two or more types of fluorescent substances or the like.

As shown in FIG. 1, the wavelength converting member 30 may be attached to the end of the light guide 20, or in other words the output region 25 in order to guide the excitation light 1, or may be attached to the connection part between the light source 10 and the light guide 20 which is the radiating part 62 for the excitation light 1. The case of the latter may be used even in locations where the tip end of the light guide will get dirty. Also, replacement of the wavelength converting member 30 will be simplified. Furthermore, productivity can be increased by establishing wavelength converting members 30 in various locations.

The wavelength conversion member 30 may be provided at some portion inside the light guide 20 by adding a fluorescent substance or the like to the core material, for example.

If the wavelength conversion member 30 is made up of a fluorescent substance, the fluorescent substance is added to a resin to produce the wavelength conversion member 30, for example. Any fluorescent substance can be used as long as it absorbs light from light source (e.g. a semiconductor light emitting element in which a nitride-based semiconductor serves as a light emitting layer), and converts the light to a different wavelength.

The fluorescent substance is preferably at least one fluorescent substance, for example, nitride or oxynitride fluorescent substances which are primarily activated by lanthanoids such as Eu or Ce, alkali earth metal halogen appetite fluorescent substances which are primarily activated by lanthanoids such as Eu or transition metal elements such as Mn, alkali earth metal borate halogen fluorescent substances, alkali earth metal aluminate fluorescent substances, alkali earth silicate fluorescent substances, alkali earth sulfide fluorescent substances, alkali earth thiogallate fluorescent substances, alkali earth nitride silicate fluorescent substances, germinate fluorescent substances, rare earth aluminate fluorescent substances which are primarily activated by lanthanoids such as Ce, rare earth silicate fluorescent substances, organic compounds and organic complexes or the like which are primarily activated by lanthanoids such as Eu. The fluorescent substance is not restricted in particular and examples of various fluorescent substances include as follows.

A nitride fluorescent substance which is primarily activated by lanthanoids such as Eu or Ce include $M_2Si_5N_8$:Eu, $MSi_7N_{10}$:Eu, $M_{1.8}Si_5O_{0.2}N_8$:Eu, and $M_{0.9}Si_7O_{0.1}N_{10}$:Eu (where M is one or more elements selected from Sr, Ca, Ba, Mg, and Zn, the same as follows).

A nitride fluorescent substance containing a Group II element M, silicon, aluminum, and nitrogen and that is activated by europium or another rare earth element will absorb from UV rays to blue light, and emit light from yellowish-red to red. This nitride fluorescent substance is expressed by the general formula: $M_wAl_xSi_yN_{((2/3)w+x+(4/3)y)}$:Eu, and contains at least one added element selected from among rare earth elements, quaternary elements, and ternary elements.

In the above general formula, the ranges of w, x, and y are preferably $0.04 \leq w \leq 9$, $x=1$, and $0.056 \leq y \leq 18$. The ranges of w, x, and y may be $0.04 \leq w \leq 3$, $x=1$, and $0.143 \leq y \leq 8.7$, and even more preferably, may be $0.05 \leq w \leq 3$, $x=1$, and $0.167 \leq y \leq 8.7$.

Boron may also be added to the nitride fluorescent substance, as in the general formula $M_wAl_xSi_yB_zN$:Eu. M, w, x and y are the same the above. When boron is added, its molar concentration z is, as seen above, 0.5 or less, and preferably 0.3 or less, and is also greater than 0.0005. Even more preferably, the molar concentration of boron is set to at least 0.001 and no more than 0.2.

These nitride fluorescent substances further contain at least one element selected from the group consisting of lanthanum, cerium, praseodymium, gadolinium, terbium, dysprosium, holmium, erbium, and lutetium, or at least one element selected from the group consisting of scandium, yttrium, gallium and indium, or either germanium and zirconium. When these are contained, brightness, quantum efficiency, or peak intensity can be equal to or better than with gadolinium, neodymium, and thulium.

An oxynitride fluorescent substance which is primarily activated by lanthanoids such as Eu or Ce includes $MSi_2O_2N_2$:Eu.

An alkali earth metal halogen appetite which is primarily activated by lanthanoids such as Eu or transition metal elements such as Mn includes $M_5(PO_4)_3X$:R (where X is one or more elements selected from F, Cl, Br, and I; and R is Eu and/or Mn, the same as follows).

An alkali earth metal borate halogen fluorescent substance includes $M_2B_5O_9X$:R or the like.

An alkali earth metal aluminate is $SrAl_2O_4$:R, $Sr_4Al_{14}O_{25}$:R, $CaAl_2O_4$:R, $BaMg_2Al_{16}O_{27}$:R, $BaMg_2Al_{16}O_{12}$:R, and $BaMgAl_{10}O_{17}$:RE or the like.

An alkali earth silicate includes $(Sr_{1-a-b-x}Ba_aCa_bEu_x)_2SiO_4$ ($0 \leq a \leq 1$, $0 \leq b \leq 1$, $0.005 \leq x \leq 0.1$) or the like.

An alkali earth sulfide includes $La_2O_2S$:Eu, $Y_2O_2S$:Eu, $Gd_2O_2S$:Eu or the like.

A rare earth aluminate which is primarily activated by lanthanoid elements such as Ce includes YAG fluorescent substance represented by $Y_3Al_5O_{12}$:Ce, $(Y_{0.8}Gd_{0.2})_3Al_5O_{12}$:Ce, $Y_3(Al_{0.8}Ga_{0.2})_5O_{12}$:Ce, $(Y,Gd)_3(Al,Ga)_5O_{12}$:Ce, as well as those where all or part of Y is replaced by Tb, Lu or the like, $Tb_3Al_5O_{12}$:Ce, $Lu_3Al_5O_{12}$:Ce or the like.

Other fluorescent substance includes ZnS:Eu, $Zn_2GeO_4$:Mn, $MGa_2S_4$:Eu or the like.

The fluorescent substances which are primarily activated by a Eu or the like are preferable, but at least one selected from a group consisting of the Tb, Cu, Ag, Au, Cr, Nd, Dy, Co, Ni, and Ti may be used in place of or in addition to Eu.

A Ca—Al—Si—O—N-based oxynitride glass fluorescent substance is a fluorescent substance in which oxynitride glass is the matrix material, and which contains 20 to 50 mol % $CaCO_3$ (calculated as CaO), 0 to 30 mol % $Al_2O_3$, 25 to 60 mol % SiO, 5 to 50 mol % AlN, and 0.1 to 20 mol % a rare earth oxide or transition metal oxide, with these five components combining for 100 mol %. With a fluorescent substance whose matrix material is oxynitride glass, the nitrogen content is preferably 15 wt % or less, and another rare earth element ion that will serve as a sensitizer besides a rare earth oxide ion is preferably contained in an amount of 0.1 to 10 mol % as a co-activator in the form of a rare earth oxide in the fluorescent glass. Besides the aforementioned fluorescent substances, other fluorescent substances which have the same performance and effect may also be used.

Reflection Member 60

The light emitting device can be provided with a reflection member 60 for reflecting at least part of the excitation light and the light emitted from the wavelength conversion member 30. Examples of the reflection member 60 include an excitation light reflection member that reflects excitation light, a wavelength-converted light reflection member that reflects light with a shorter wavelength than that near the emission peak wavelength of the wavelength conversion member, and a UV light reflection member that reflects light in the UV band.

Figure 3:
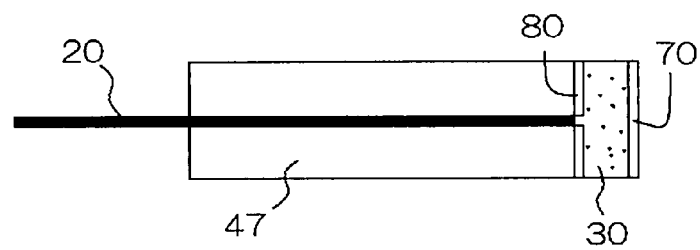
FIG. 3 is a detail view of the other exit section 25 in FIG. 1.

As shown in FIG. 3, the reflection member 60 need not be provided. In this case, the light guide end member 47 is provided to the end on the emission side of the light guide 20, and the reflective film 80 that reflects light of a specific wavelength band is formed at the end face of this light guide end member 47. Also, in the configuration shown in FIG. 3, the wavelength conversion member 30 is attached to the light guide end member 47 with the reflective film 80 sandwiched in between, and the shielding member 70 is attached to the emission side of the wavelength conversion member 30.

Excitation Light Reflection Member

The excitation light reflecting member can be used to prevent the excitation light from radiating directly to the outside or to prevent the excitation light from leaking to unintended areas. Thereby, excitation light which has passed through the wavelength converting member but was not wavelength converted by the fluorescent substance or the like can be returned back to the wavelength converting member in order to increase the light emitting efficiency. Therefore, the excitation light reflecting member is preferably formed from a material which allows transmission of only light of a specific wavelength which has been wavelength converted but reflects excitation light. Furthermore, the excitation light reflecting member is preferably located at least on the wavelength converted light emission region of the wavelength converting member, as shown in FIG. 2. Thereby radiation of excitation light to the outside can be reduced and the light emitting efficiency can be increased.

Wavelength-Converted Light Reflecting Member

The wavelength-converted light reflecting member prevents wavelength converted light from the wavelength converting member from returning to the excitation light incidence side and also can be used to externally discharge by reflecting light which has returned to the excitation light incidence side. Therefore, the wavelength-converted light reflecting member is preferably formed from a material which can transmit only certain wavelengths of light while reflecting certain wavelengths, or in other words, wavelength converted light. Thereby the light which returns to the excitation light incidence side can be reflected and the light emitting efficiency can be increased. As shown in FIG. 2, the reflecting member is located on the wavelength converted light output region, but the wavelength converted light reflecting member is preferably located at least on the excitation light incidence region of the wavelength converting member.

UV Light Reflection Member

With a UV light reflection member, even if a light emitting element that emits UV rays is used for the light source, the UV rays can be reflected and no emitted from the light emitting device, so a light emitting device that is safer for humans and the environment can be obtained.

Shielding Member 70

With this light emitting device, the shielding member 70 is provided on the emission side of the wavelength conversion member 30, and this shielding member 70 blocks (or absorbs and/or reflects) at least part of the excitation light and the light emitted from the wavelength conversion member 30, and transmits the light other than the light that is blocked (or absorbed and/or reflected) by the shielding member. This allows just light of a specific wavelength to be taken out. For example, if blue light (445 nm) is emitted from the laser diode of the light source 10, and an LAG fluorescent substance $(Lu_3Al_5O_{12}:Ce)$ is used for the wavelength conversion member 30, cyan light will be emitted from the light emitting device as a whole, but if the above-mentioned shielding member 70 is used to cut out light under 445 nm, green light over 445 nm can be obtained. As a result, a light emitting device that emits green light can be obtained even though no light emitting element that emits green light has been developed, and even if a light emitting element that emits green cannot be utilized for some reason.

Also, with the shielding member 70, UV rays can be blocked even when the light source 10 is a light emitting element that emits UV rays, so a light emitting device that is safer for humans and the environment can be obtained.

Furthermore, a diffusion member, which is used to increase emission efficiency mainly by diffusing excitation light, can be contained in the shielding member 70. Doing this reduces unevenness in the color of the light emitted from the light emitting device. This diffusion member is preferably one of the above-mentioned resins with a relatively high refractive index, the product of adding the above-mentioned filler to the above-mentioned resin, or the like. It is especially favorable to use a silicone resin that contains a filler.

Furthermore, the orientation of the light emitted from the light emitting device will be more consistent if the shielding member 70 is formed in the shape of a lens.

Because the light emitting device in this embodiment is equipped with the shielding member 70 and the reflection member 60, a light emitting device that emits green light can be obtained even though no light emitting element that emits green light has been developed, and even if a light emitting element that emits green cannot be utilized for some reason. With the light emitting device pertaining to this embodiment, light under 445 nm, including the UV band, can be reflected, and the reflected light hits the wavelength conversion member 30, affording an increase in excitation efficiency.

The above description is given for the purpose of embodying the technological concept of the present invention, and is not intended to limit the present invention.

Figure 15:
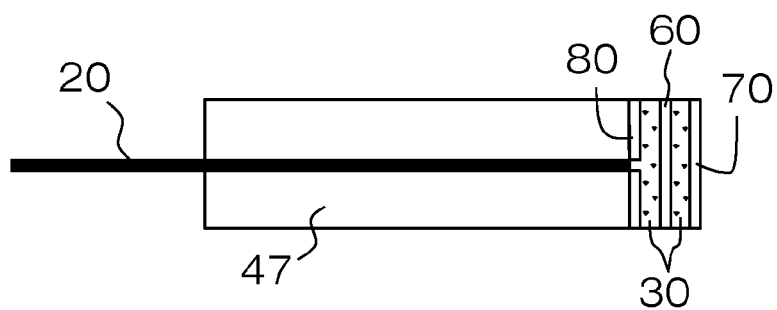
FIG. 15 is a detail view of the exit section 25 according to another embodiment.

For instance, the shielding member and reflection member discussed above are not limited to being provided to the light guide end member or the wavelength conversion member or the shielding member, and can be provided at any suitable location. The light guide end member, the wavelength conversion member, the shielding member, and the reflection member can also be provided such that they are spatially separated. Also, as shown is FIG. 15, if the wavelength conversion member is made up of two or more layers, the shielding member or the reflection member can be provided sandwiched in between these layers, as doing this will improve excitation efficiency.

Also, as shown in FIG. 1, the light emitting device of the present invention may comprise a single light source 10, a single light guide 20, and a single wavelength conversion member 30, and a plurality of these single unit light emitting devices may be installed to produce a light emitting device.

The device may comprise a plurality of light guides and corresponding wavelength conversion members for a single light source. Or, there may be a plurality of light guides for a single light source, and the light from these light guides may undergo wavelength conversion by a single wavelength conversion member. Alternatively, there may be a corresponding plurality of light guides for a plurality light source, and the light from these light guides may undergo wavelength conversion by a single wavelength conversion member. These light emitting devices may also be combined into a single light emitting device.

Embodiment 2

Figure 4:
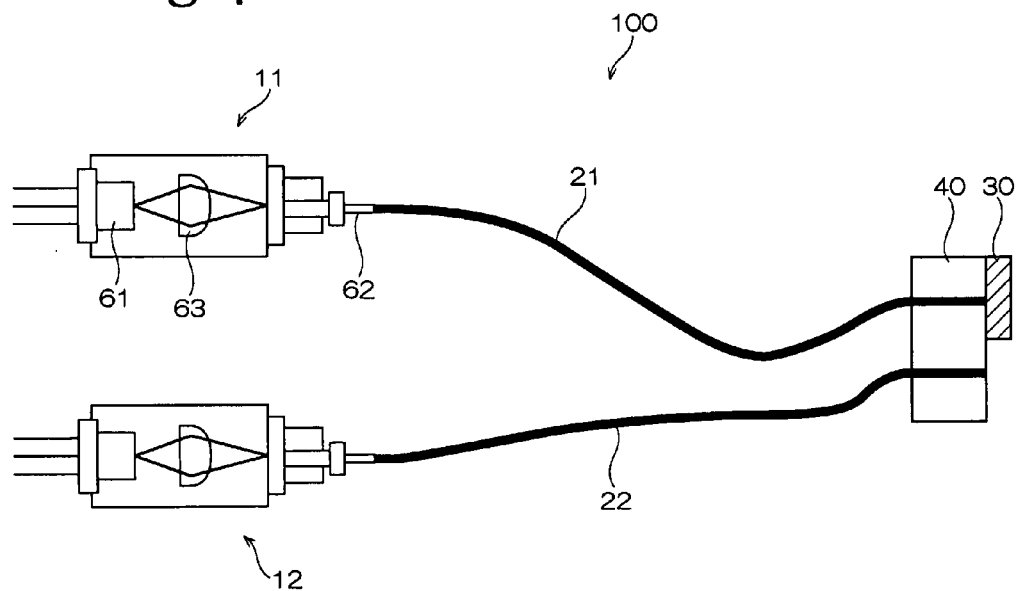
FIG. 4 is a simplified diagram of the light emitting device pertaining to Embodiment 2 of the present invention.

As shown in FIG. 4, the light emitting device 100 of the embodiment comprises a first light source 11, with an emission peak wavelength in a wavelength band of 400 to 500 nm, a second light source 12, with an emission peak wavelength in a wavelength band of 600 to 700 nm, a first light guide 21 having at least one optical fiber for propagating the light emitted by the first light source 11, in which the refractive index of the center part (core) of a cross section is higher than the refractive index of the peripheral part (cladding), a second light guide 22 having at least one optical fiber for propagating the light emitted by the second light source 12, a wavelength conversion member 30 that is provided to just the end on the emission side of the first light guide 21, absorbs the light propagated by the first light guide 21 and converts the wavelength thereof, and releases light having an emission peak wavelength in a wavelength band of 450 to 650 nm.

With the light emitting device 100 pertaining to this embodiment, the light emitted from a first light source 11, with an emission peak wavelength in a wavelength band of 400 to 500 nm, propagates through a first light guide 21 and is incident on the wavelength conversion member 30. At the wavelength conversion member 30, part of the incident light is wavelength-converted into light having an emission peak wavelength in a wavelength band of 450 to 650 nm, and this is combined with the light that did not undergo wavelength conversion and still has an emission peak wavelength in a wavelength band of 400 to 500 nm, and this mixed light is emitted from the light emitting device 100. The light emitted from a second light source 12, with an emission peak wavelength in a wavelength band of 600 to 700 nm, is emitted from the light emitting device 100 without passing through the wavelength conversion member 30.

This light emitting device 100 differs from the above-mentioned conventional projector device in which a fluorescent substance is added to the core of an optical fiber, in that the wavelength conversion member 30 is provided to the end of the first light guide 21. Therefore, leakage of wavelength-converted light from the light guides can be prevented, and the light flux can be increased.

Also, the multi-fiber light guide end member 40 is provided to the ends on the emission side of the first light guide 21 and a second light guide 22. This has the effect of reducing the size of the emitted light spot.

Embodiment 3

Figure 5:
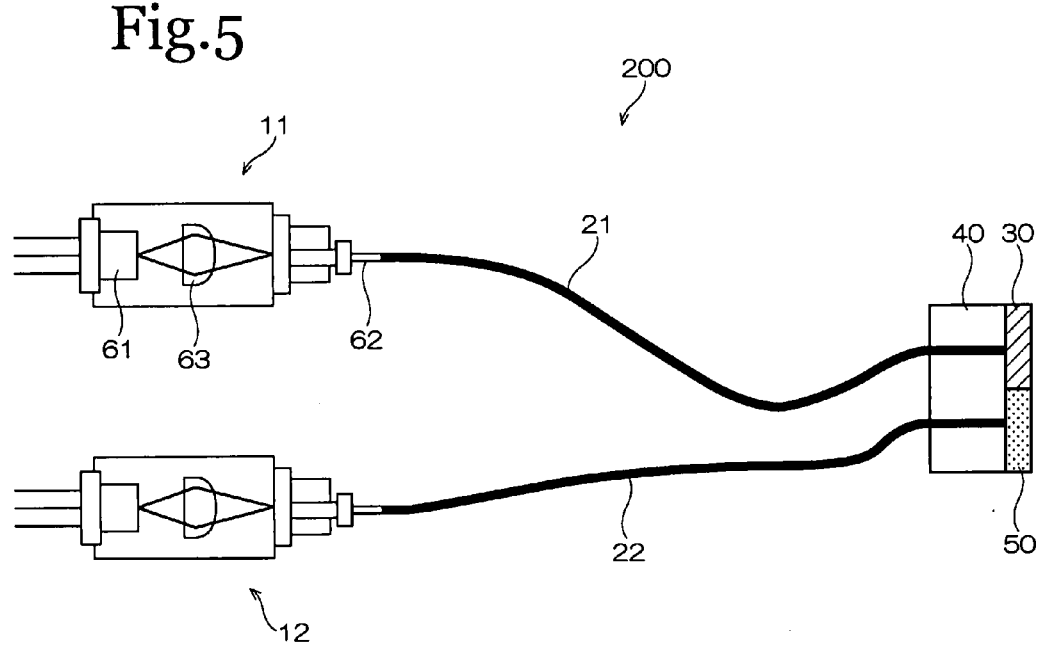
FIG. 5 is a simplified diagram of the light emitting device pertaining to Embodiment 3 of the present invention.

As shown in FIG. 5, this light emitting device 200 differs from the light emitting device 100 pertaining to the first embodiment in that a diffusion material 50 is provided to the end on the emission side of the second light guide 22. Doing this reduces unevenness in the color of the light emitted from the light emitting device 200.

The diffusion material 50 is a resin, for example, and preferably one with a relatively high refractive index, the product of adding the above-mentioned filler to the above-mentioned resin, or the like. It is especially favorable to use a silicone resin that contains a filler.

Embodiment 4

Figure 6:
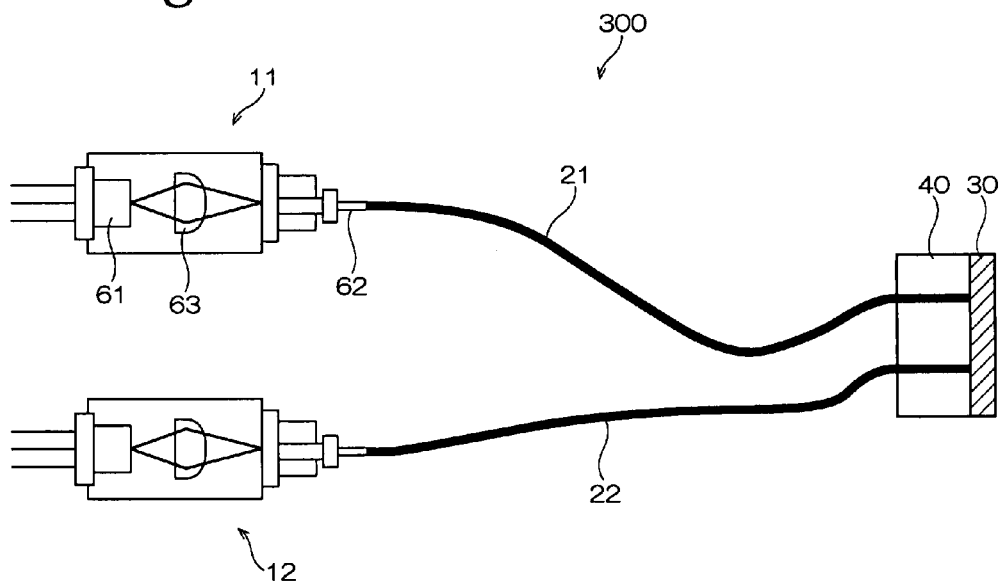
FIG. 6 is a simplified diagram of the light emitting device pertaining to Embodiment 4 of the present invention.

As shown in FIG. 6, this light emitting device 300 differs from the light emitting device 100 pertaining to the first embodiment in that the wavelength conversion member 30 is provided to the end on the emission side of the second light guide 22. The wavelength conversion member provided to the end on the emission side of the first light guide 21 can be separate from the wavelength conversion member provided to the end on the emission side of the second light guide 22, but these are preferably provided integrally as shown in FIG. 6. This facilitates manufacture and reduces the amount of wavelength conversion member 30 needed. Also, if the members are separate, color evenness may result from differences in the amounts of the two, and integrating the two components affords a reduction in color unevenness and makes it easier to achieve uniform thickness and amounts between the portion at the end on the emission side of the first light guide 21 and the portion at the end on the emission side of the second light guide 22.

Embodiment 5

Figure 7:
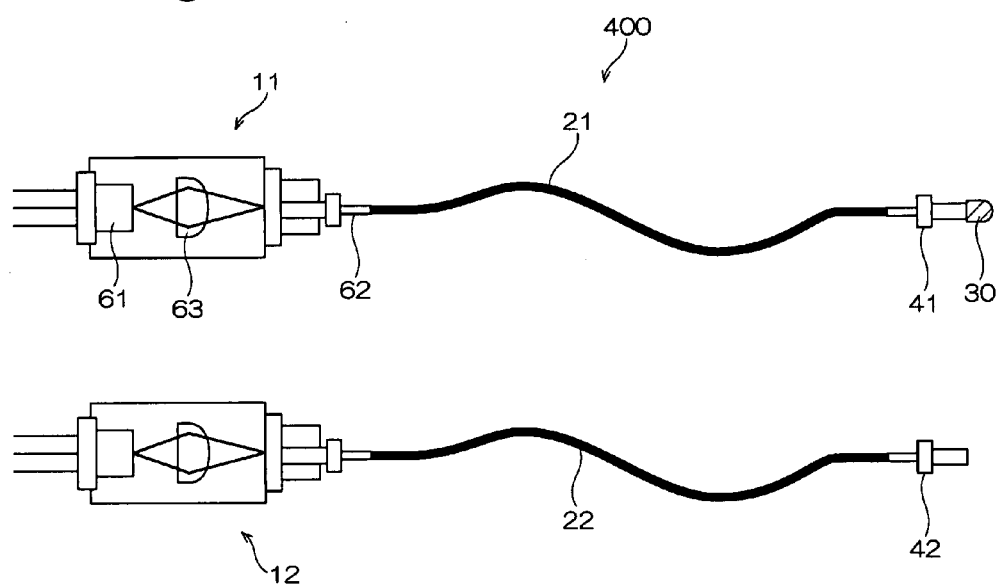
FIG. 7 is a simplified diagram of the light emitting device pertaining to Embodiment 5 of the present invention.

As shown in FIG. 7, this light emitting device 400 differs from the light emitting device 100 pertaining to the first embodiment in that it comprises a single-fiber first light guide end member 41 at the end on the emission side of the first light guide 21, and a single-fiber second light guide end member 42 at the end on the emission side of the second light guide 22. With this light emitting device 400, the first light guide 21 and the second light guide 22 are disposed such that light emitted from the first light guide 21 and light emitted from the second light guide 22 undergo color mixing at the emission face. This has the effect of increasing the mounting yield as compared to when a multi-fiber light guide end member is used.

Embodiment 6

Figure 8:
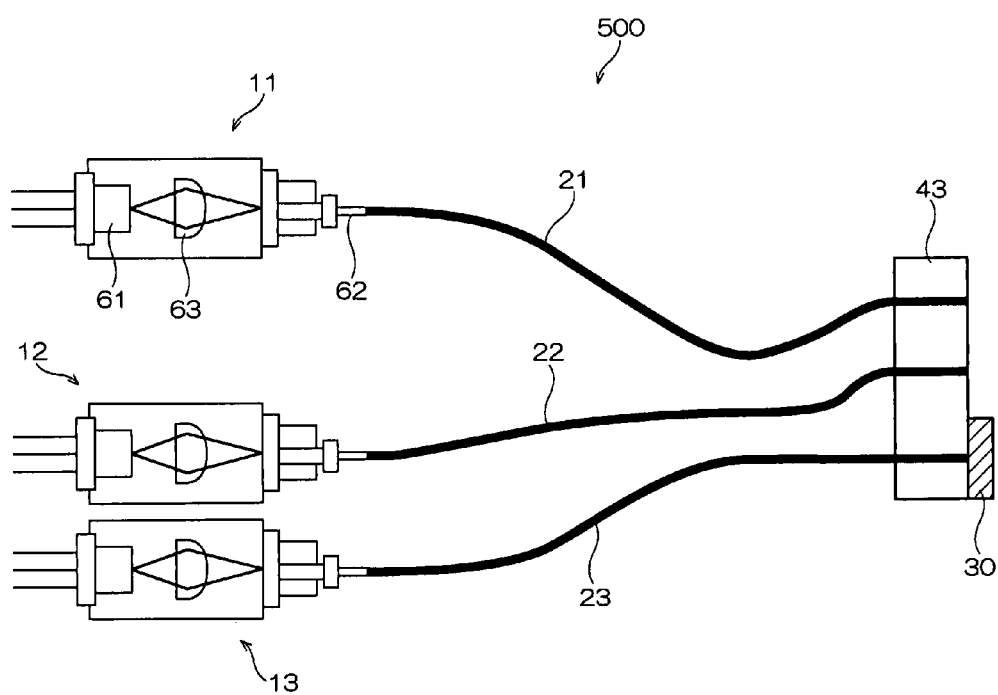
FIG. 8 is a simplified diagram of the light emitting device pertaining to Embodiment 6 of the present invention.

As shown in FIG. 8, the light emitting device 500 of the embodiment comprises a first light source 11, with an emission peak wavelength in a wavelength band of 400 to 500 nm, a second light source 12, with an emission peak wavelength in a wavelength band of 600 to 700 nm, a third light source 13, with an emission peak wavelength in a wavelength band of 300 to 400 nm, a first light guide 21 having at least one optical fiber for propagating the light emitted by the first light source 11, in which the refractive index of the center part (core) of a cross section is higher than the refractive index of the peripheral part (cladding), a second light guide 22 having at least one optical fiber for propagating the light emitted by the second light source 12, in which the refractive index of the center part (core) of a cross section is higher than the refractive index of the peripheral part (cladding), a third light guide 23 having at least one optical fiber for propagating the light emitted by the third light source 13, in which the refractive index of the center part (core) of a cross section is higher than the refractive index of the peripheral part (cladding), a wavelength conversion member 30 that is provided to just the end on the emission side of the third light guide 23, absorbs the light propagated by the third light guide 23 and converts the wavelength thereof, and releases light having an emission peak wavelength in a wavelength band of 450 to 650 nm.

With this light emitting device 500, the light having an emission peak wavelength in a wavelength band of 300 to 400 nm emitted from a third light source 13 is subjected to wavelength conversion by the wavelength conversion member 30, and becomes light having an emission peak wavelength in a wavelength band of 450 to 650 nm, which is a longer wavelength than the above-mentioned emission peak wavelength. Generally, the light emitted from the third light source 13 in a wavelength band of 300 to 400 nm is difficult to perceive visually. Thus, the light color is not mixed well, and color unevenness tends to occur. However, with this light emitting device, the light from the wavelength conversion member 30 can be mainly what is visually perceived.

When a light emitting device is used for illumination or for medical purposes, a filter that cuts out the light in a wavelength band of 400 nm or less emitted from the third light source 13 is preferably provided to the end on the emission side of the wavelength conversion member 30 or the light guide.

A multi-fiber light guide end member 43 is provided to the end on the emission side of the first light guide 21, the second light guide 22, and a third light guide 23. This has the effect of reducing the size of the emitted light.

Embodiment 7

Figure 9:
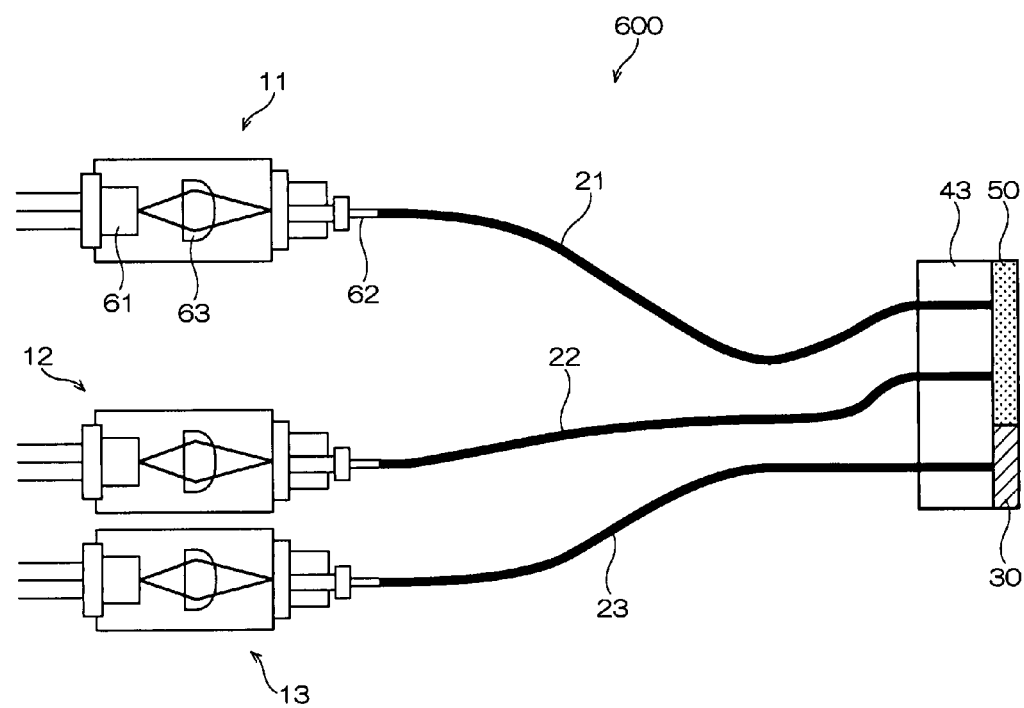
FIG. 9 is a simplified diagram of the light emitting device pertaining to Embodiment 7 of the present invention.

As shown in FIG. 9, this light emitting device 600 differs from the light emitting device 500 pertaining to the sixth embodiment in that the diffusion member 50 is provided to the end on the emission side of the first light guide 21 and to the end on the emission side of the second light guide 22.

This has the effect of matching up the orientation of the emitted light.

Embodiment 8

Figure 10:
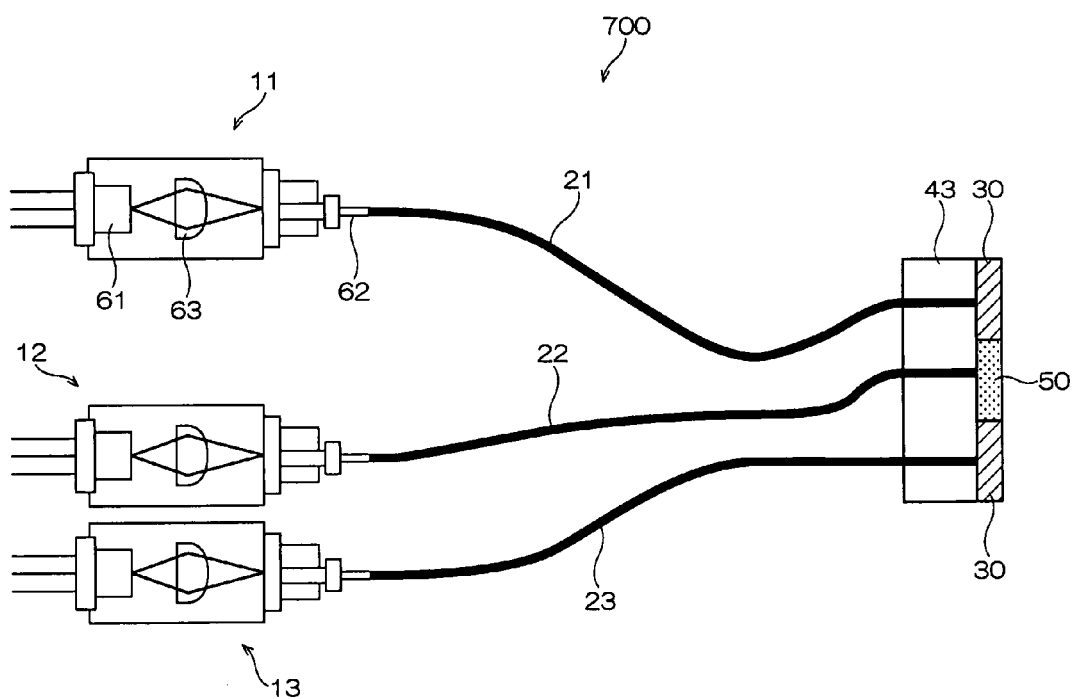
FIG. 10 is a simplified diagram of the light emitting device pertaining to Embodiment 8 of the present invention.

As shown in FIG. 10, this light emitting device 700 differs from the light emitting device 600 pertaining to the seventh embodiment in that the wavelength conversion member 30 is provided to the end on the emission side of the first light guide 21.

It affords an increase in the amount of the wavelength conversion member 30.

Embodiment 9

Figure 11:
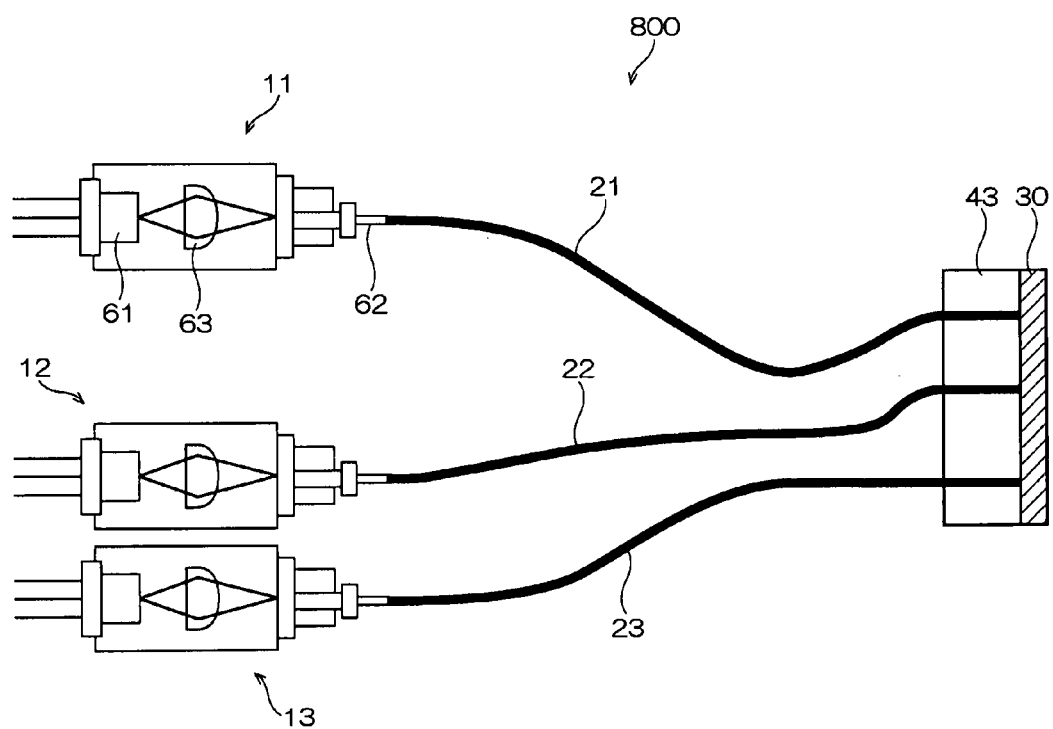
FIG. 11 is a simplified diagram of the light emitting device pertaining to Embodiment 9 of the present invention.

As shown in FIG. 11, this light emitting device 800 differs from the light emitting device 500 and 600 pertaining to the sixth and seventh embodiments in that the wavelength conversion member 30 is provided to the end on the emission side of the first light guide 21 to the third light guide 23.

It affords an increase in the amount of the wavelength conversion member 30.

Embodiment 10

Figure 12:
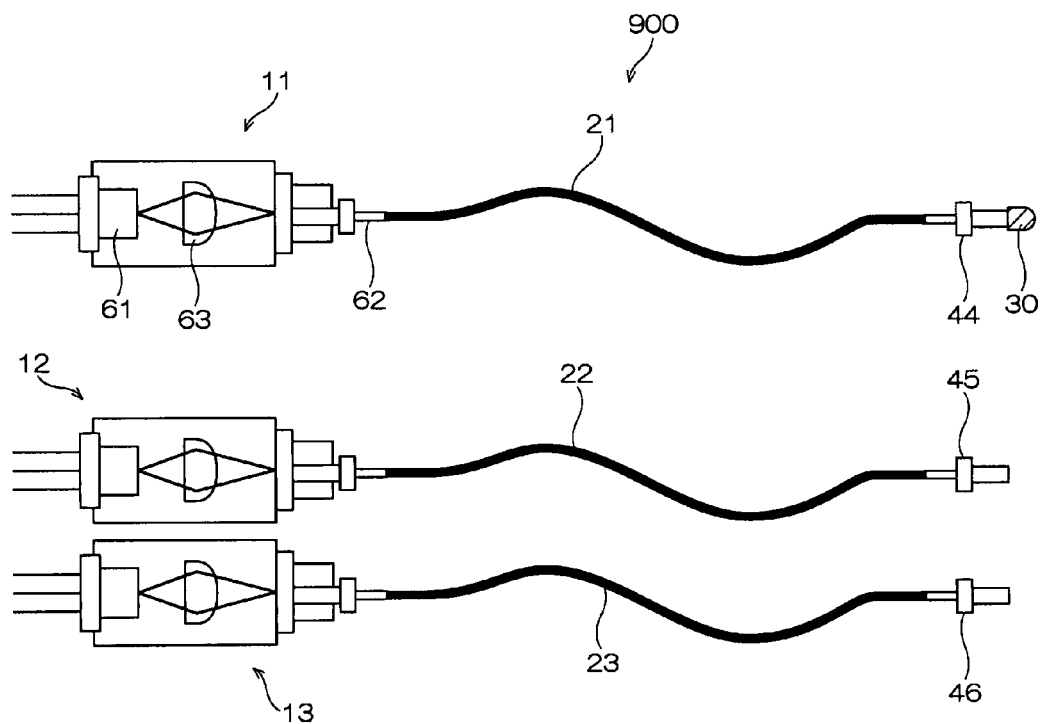
FIG. 12 is a simplified diagram of the light emitting device pertaining to Embodiment 10 of the present invention.

As shown in FIG. 12, this light emitting device 900 differs from the light emitting devices 500, 600, and 700 pertaining to the sixth, seventh, and eighth embodiments in that a single-fiber first light guide end member 44 is provided at the end on the emission side of the first light guide 21, a single-fiber second light guide end member 45 is provided at the end on the emission side of the second light guide 22, and a single-fiber third light guide end member 46 is provided at the end on the emission side of the third light guide 23.

With this light emitting device 900, the first light guide 21, the second light guide 22, and the third light guide 23 are disposed such that light emitted from the first light guide 21, light emitted from the second light guide 22, and light emitted from the third light guide 23 undergo color mixing at the emission face. This has the effect of increasing the mounting yield as compared to when a multi-fiber light guide end member is used.

The first to third light sources may also each be constituted by a plurality of light sources. Also, the first to third light guides may each be constituted by a plurality of light guides. A plurality of light guides and corresponding wavelength conversion members may be used for a single light source. Also, there may be a plurality of light guides for a single light source, and the light from these light guides may undergo wavelength conversion by a single wavelength conversion member. Furthermore, there may be a plurality of light sources and a plurality of light guides corresponding to these light sources, and the light from these light guides may undergo wavelength conversion by a single wavelength conversion member. These light emitting devices may also be combined into a single light emitting device.

The above-mentioned reflection members (such as an excitation light reflection member, wavelength-converted light reflection member, or UV light reflection member), shielding members, and so forth may be used in combinations as discussed above, in the second to tenth embodiments.

EXAMPLE 1

Green light was obtained using a laser diode that emitted light of 445 nm as a light emitting element of a light source, using a wavelength conversion member containing LAG ($Lu_3Al_5O_{12}$:Ce), and using a dielectric multilayer film that blocked light of 445 nm as a shielding member.

EXAMPLE 2

Green light with a high y value was obtained using a laser diode that emitted light of 445 nm as a light emitting element of a light source, using a wavelength conversion member containing LAG ($Lu_3Al_5O_{12}$:Ce), using as a shielding member a dielectric multilayer film that transmitted a green component with a high y value (at chromaticity diagram) and reflected other components, and using a reflective film that reflected light of a specific wavelength band (a reflective film that reflected light that had been emitted from a light guide and then was about to be incident on the light guide again).

EXAMPLE 3

A laser diode that emitted light of 405 nm was used as a light emitting element of a light source, a wavelength conversion member containing CCA+YAG (two stacked layers, from the light source side) was provided, and a dielectric multilayer film that reflected light of 405 nm was used as a shielding member. With light of 405 nm, CCA can be excited, but not YAG. In view of this, excitation efficiency can be improved by providing a reflection member that reflects light of 405 nm between the CCA and YAG. CCA is an alkaline earth halogen appetite activated by europium, i.e. $Ca_5(PO_4)_3Cl$:Eu. Also, YAG is rare earth aluminates which is primarily activated by Ce, for example, $Y_3Al_5O_{12}$:Ce (as well as those where part of Y is replaced by Gd and/or those where part of the Al is replaced by Ga).

EXAMPLE 4

Green light with a high y value was obtained using a laser diode that emitted light of 405 nm as a light emitting element of a light source, using a wavelength conversion member containing strontium thiogallate, and using as a shielding member a dielectric multilayer film that removed a green component with a low y value. Efficiency here can be further increased by reflecting light of 405 nm with a dielectric multilayer film that is a shielding member. Strontium thiogallate is $SrGa_2S_4$:Eu.

EXAMPLE 5

A laser diode that emitted light of 445 nm was used as a light emitting element of a light source, a wavelength conversion member containing LAG+CASBN (two stacked layers, from the light source side) was provided, and a dielectric multilayer film that transmitted part and reflected part of the light of 445 nm was used as a shielding member, whereupon the transmitted light was part of the white light, the reflected light was used as an excitation light source for the wavelength conversion member, and the overall emission efficiency increased. LAG is $Lu_3Al_5O_{12}$:Ce, and CASBN is $CaAlSiB_{0.005}N_{3.005}$:Eu.

EXAMPLE 6

Figure 13:
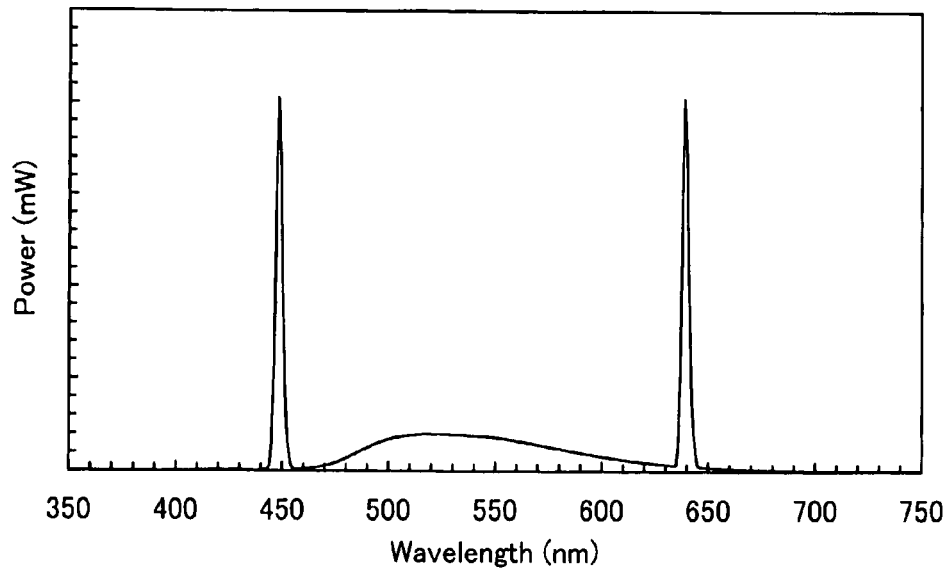
FIG. 13 is a graph of the results of simulating the frequency spectrum emitted from the light emitting device pertaining to Embodiment 2.

FIG. 13 is a graph of the results of simulating the frequency spectrum emitted from the light emitting device pertaining to the first embodiment.

As shown in FIG. 13, in this simulation, the light emitting device pertaining to the first embodiment emits white light in which blue, green, and red light is mixed. More specifically, in a simulation in which a light source emitting blue light with an emission peak wavelength of about 450 nm was used as a first light source and a light source emitting red light with an emission peak wavelength of about 640 nm was used as a second light source, the light emitting device emitted blue light with an emission peak wavelength of about 450 nm, red light with an emission peak wavelength of about 640 nm, and green light with an emission peak wavelength of 450 to 650 nm.

EXAMPLE 7

Figure 14:
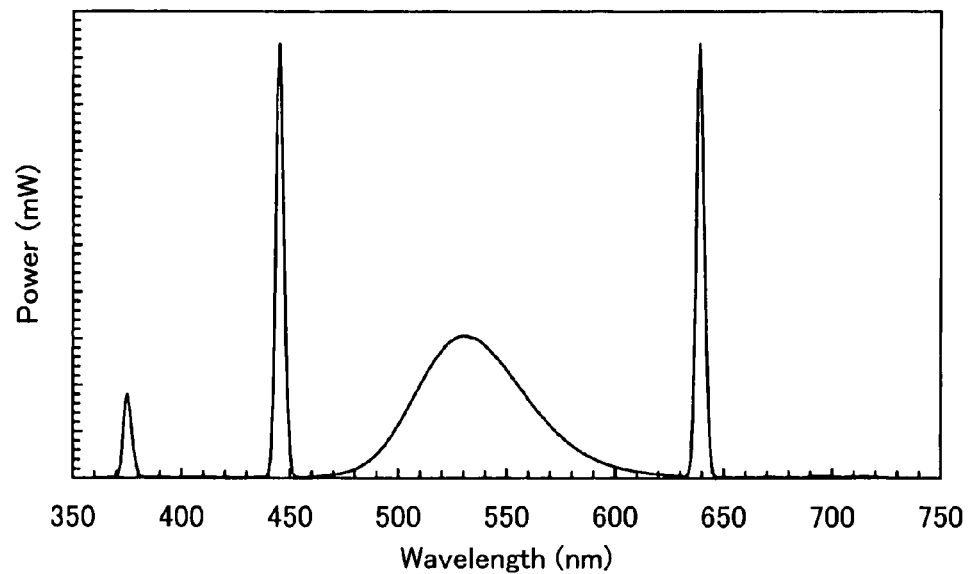
FIG. 14 is a graph of the results of simulating the frequency spectrum emitted from the light emitting device pertaining to Embodiment 6.

FIG. 14 is a graph of the results of simulating the frequency spectrum emitted from the light emitting device pertaining to the sixth embodiment.

As shown in FIG. 14, in this simulation, the light emitting device pertaining to the fifth embodiment emits white light in which UV, blue, green, and red light is mixed. More specifically, in a simulation in which a light source emitting blue light with an emission peak wavelength of about 450 nm was used as a first light source, a light source emitting red light with an emission peak wavelength of about 640 nm was used as a second light source, and a light source emitting UV light with an emission peak wavelength of about 375 nm was used as a third light source, the light emitting device emitted blue light with an emission peak wavelength of about 450 nm, red light with an emission peak wavelength of about 640 nm, UV light with an emission peak wavelength of about 375 nm, and green light with an emission peak wavelength of 450 to 650 nm.

The light emitting device of the present invention with can be utilized in projector devices, lighting fixture, automotive lighting, laser display, indicator, and so forth. Furthermore, the device may also be utilized as an endoscope for observing inside a living body, as a fiber scope for observing inside extremely narrow or dark spaces, and as a light source for various industrial, construction in members where current leak and heating or the like are to be avoided.

This application claims priority to Japanese Patent Application Nos. 2006-36258 and 2006-81524. The entire disclosure of Japanese Patent Application Nos. 2006-36258 and 2006-81524 are hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A light emitting device comprising:
   a light source that emits excitation light;
   a light guide that propagates the excitation light, and in which the refractive index of the center part of a cross section is higher than the refractive index of the peripheral part;
   a light guide end member supporting an end of an emission side of the light guide and covering an outer circumference of the light guide;
   a wavelength conversion member including a fluorescent substance that absorbs the excitation light propagated by the light guide and converts the wavelength thereof, and releases light of a predetermined wavelength band;
   a shielding member that blocks the wavelength of at least part of the excitation light and the light emitted from the wavelength conversion member, the shielding member being disposed on a first side of the wavelength conversion member and the light guide being disposed on a second side of the wavelength conversion member that is different from the first side; and
   a reflection member that reflects at least part of the excitation light and the light emitted from the wavelength conversion member, the reflection member including a reflective film that reflects light of a predetermined wavelength band with the reflective film being formed at an end face of the light guide end member, wherein
   the wavelength conversion member is coupled to a tip end of the light guide on the second side of the wavelength conversion member with the reflection member being sandwiched between the light guide and the wavelength conversion member.

2. The light emitting device according to claim 1, wherein the reflection member reflects light with a shorter wavelength than that near the emission peak wavelength of the wavelength conversion member.

3. The light emitting device according to claim 2, wherein the reflection member reflects light with a wavelength of about 420 nm or less.

4. The light emitting device according to claim 1, wherein the reflection member includes an excitation light reflecting member arranged at least on a wavelength converted light emission region of the wavelength converting member.

5. The light emitting device according to claim 1, wherein the shielding member is attached to an emission side of the reflection member.

6. The light emitting device according to claim 1, wherein at least one of the shielding member and the reflection member is in contact with the wavelength conversion member.

7. The light emitting device according to claim 1, wherein the wavelength conversion member includes a resin layer containing the fluorescent substance.

8. The light emitting device according to claim 1, wherein the shielding member is configured and arranged to allow only light having a prescribed wavelength to pass through.

9. A light emitting device comprising:
   a light source that emits excitation light;

a light guide that propagates the excitation light, and in which the refractive index of the center part of a cross section is higher than the refractive index of the peripheral part;

a wavelength conversion member including a fluorescent substance that absorbs the excitation light propagated by the light guide and converts the wavelength thereof, and releases light of a predetermined wavelength band;

a shielding member disposed fully downstream of an end of an emission side of the light guide with respect to a propagation direction of the light, and that blocks the wavelength of at least part of the excitation light and the light emitted from the wavelength conversion member; and a reflection member that reflects at least part of the excitation light and the light emitted from the wavelength conversion member, wherein the shielding member is in the form of a lens.

10. The light emitting device according to claim 9, wherein the shielding member includes a diffusion member.

11. The light emitting device according to claim 9, wherein the reflection member includes an excitation light reflecting member arranged at least on a wavelength converted light emission region of the wavelength converting member.

12. The light emitting device according to claim 9, wherein the reflection member includes a wavelength-converted light reflecting member arranged at least on an excitation light incidence region of the wavelength converting member.

13. The light emitting device according to claim 9, wherein the shielding member is attached to an emission side of the reflection member.

14. The light emitting device according to claim 9, wherein at least one of the shielding member and the reflection member is in contact with the wavelength conversion member.

15. The light emitting device according to claim 9, wherein the wavelength conversion member includes a resin layer containing the fluorescent substance.

16. The light emitting device according to claim 9, wherein the shielding member is configured and arranged to allow only light having a prescribed wavelength to pass through.

17. A light emitting device comprising:

a light source that emits excitation light;

a light guide that propagates the excitation light, and in which the refractive index of the center part of a cross section is higher than the refractive index of the peripheral part;

a wavelength conversion member including a fluorescent substance that absorbs the excitation light propagated by the light guide and converts the wavelength thereof, and releases light of a predetermined wavelength band;

a shielding member that blocks the wavelength of at least part of the excitation light and the light emitted from the wavelength conversion member; and a reflection member that reflects at least part of the excitation light and the light emitted from the wavelength conversion member, wherein the wavelength conversion member is made up of two or more layers, and the reflection member is sandwiched between the layers of the wavelength conversion member.

* * * * *